United States Patent [19]

Koebernick et al.

[11] 4,429,117

[45] Jan. 31, 1984

[54] PROCESS FOR THE PRODUCTION OF KNOWN AND NEW 6-AMINO-6-DESOXY-2,3-O-ISOPROPYLI-DENE-α-L-SORBOFURANOSE DERIVATIVES, AND INTERMEDIATE PRODUCTS OF THE PROCESS

[75] Inventors: Wolfgang Koebernick; Hans-Rolf Furtwängler, both of Wuppertal, Fed. Rep. of Germany

[73] Assignee: Bayer Aktiengesellschaft, Leverkusen, Fed. Rep. of Germany

[21] Appl. No.: 180,778

[22] Filed: Aug. 25, 1980

[30] Foreign Application Priority Data

Sep. 7, 1979 [DE] Fed. Rep. of Germany ....... 2936240

[51] Int. Cl.$^3$ ............................................. C07H 17/04
[52] U.S. Cl. .................................. 536/17.2; 536/17.5; 536/55; 536/55.3; 536/124; 546/219; 546/242
[58] Field of Search .................. 536/4, 18, 17.2, 17.5, 536/55, 55.3, 124

[56] References Cited

U.S. PATENT DOCUMENTS

| | | | |
|---|---|---|---|
| 2,422,997 | 6/1947 | Wuest | 536/18 |
| 2,884,411 | 4/1959 | Heyns | 536/18 |
| 4,220,782 | 9/1980 | Stoltefuss | 536/4 |
| 4,260,622 | 4/1981 | Junge et al. | 536/18 |

*Primary Examiner*—Johnnie R. Brown
*Attorney, Agent, or Firm*—Sprung, Horn, Kramer & Woods

[57] ABSTRACT

The invention relates, inter alia, to a process for the provision of 6-amino-6-desoxy-2,3-O-isopropylidene-α-L-sorbofuranose derivatives which comprises treating a 2,3-O-isopropylidene-6-sulphonated-α-L-sorbofuranase with an amine in an aqueous medium in an autoclave, followed by reaction of the reactions product in a basic medium to provide the free amine of Formula I as described hereinafter. The invention also includes the products obtained by the reaction and the invention further includes the process for providing the compounds of Formula VII as described hereinafter by treatment of a compound of Formula I as described hereinafter with an acid, followed by hydrogenation. The products of the invention are useful as medicaments or intermediates for medicaments.

5 Claims, No Drawings

PROCESS FOR THE PRODUCTION OF KNOWN AND NEW 6-AMINO-6-DESOXY-2,3-O-ISOPROPYLIDENE-α-L-SORBOFURANOSE DERIVATIVES, AND INTERMEDIATE PRODUCTS OF THE PROCESS

The present invention relates to a chemically unobvious process for the production of certain 6-amino-6-desoxy-2,3-O-isopropylidene-α-L-sorbofuranose derivatives, and to novel intermediate products of the process.

It is known that 6-amino-6-desoxy-2,3-O-isopropylidene-α-L-sorbofuranose is obtained when 6-azido-6-desoxy-2,3-O-isopropylidene-α-L-sorbofuranose is hydrogenated with hydrogen in the presence of Raney nickel (see H. Paulsen, J. Sangster and K. Heyns, Chem. Ber. 100 (1967) 802–815). The disadvantages of this process are that the 2,3-O-isopropylidene-6-O-tosyl-α-L-sorbofuranose used as the starting material is very unstable and cannot be handled in relatively large amounts, and that, because of the azido group, 6-azido-6-desoxy-2,3-O-isopropylidene-α-L-sorbofuranose tends to undergo spontaneous exothermic decomposition and is thus unsuitable for carrying out the process on a large industrial scale. Further disadvantages of the process are the high number of reaction stages and the low yield associated therewith.

It is furthermore known that 6-amino-6-desoxy-2,3,-O-isopropylidene-α-L-sorbofuranose can be obtained by heating 2,3-O-isopropylidene-6-O-tosyl-α-L-sorbofuranose in liquid ammonia for 10 days (see K. Tokujama, M. Kiyokawa and N. Hoki, Bull. Chem. Soc. Japan 36 (1963) 1392–1395). However, in this process, the desired product cannot be isolated directly, but must first be converted into the corresponding N-benzoyl compound with p-nitrobenzoyl chloride and the N-benzoyl compound is purified and then split to give the desired product.

According to the present invention there is provided a process for the production of a 6-amino-6-desoxy-2,3-O-isopropylidene-α-L-sorbofuranose derivative of the formula

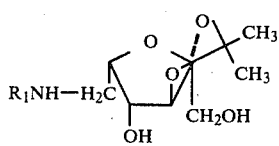

(I)

in which
$R_1$ denotes a hydrogen atom or an optionally substituted alkyl, alkenyl, alkinyl or alkadienyl radical,
in which a compound of the general formula

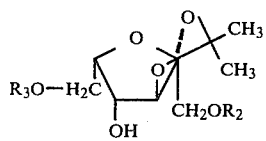

(II)

in which
$R_2$ denotes a hydrogen atom or an acyl radical and
$R_3$ denotes a radical of an aliphatic or aromatic sulphonic acid,
is heated with an amine of the general formula $$R_1-NH_2 \quad (III)$$

wherein
$R_1$ has the abovementioned meaning,
in an aqueous medium in an autoclave, and the reaction product is reacted in a basic medium to give the free amine of formula (I), preferably by reaction with a base or a basic ion exchanger in water at room temperature to 100° C. for 10 minutes to 2 hours.

$R_1$ preferably denotes an optionally substituted alkyl radical with 1 to 30, in particular 1 to 18, carbon atoms or an alkenyl, alkinyl or alkadienyl radical with 2 to 18, in particular 2 to 10 carbon atoms.

Examples of substituents for alkyl which may be mentioned are: hydroxyl; alkoxy with 1 to 4 carbon atoms; acyloxy (the acyl radical being derived from aliphatic, particularly alkane, carboxylic acids with 1 to 7 carbon atoms), aromatic carboxylic acids (preferably phenylcarboxylic acids, which are optionally substituted in the phenyl radical by hydroxyl, halogen, $C_1$ to $C_4$ alkyl, $C_1$ to $C_4$ alkoxy, nitro or amino), or heterocyclic carboxylic acids derived from 5-membered or 6-membered heterocyclic compounds which contain 1 to 3 hetero-atoms selected from N, O and S are optionally substituted in the heterocyclic ring by $C_1$ to $C_4$ alkyl, chlorine, bromine or amino; amino or mono- or dialkylamino with preferably 1 to 4 carbon atoms per alkyl radical; monoacylamino, acyl having the abovementioned meaning; mercapto; $C_1$ to $C_4$ alkylthio; halogen; $C_1$ to $C_4$ alkylcarbonyl; carboxyl; nitro; cyano; formyl; sulpho; heterocyclyl having the abovementioned definition; $C_3$ to $C_7$ cycloalkyl; and phenyl which is optionally substituted by halogen, $C_1$ to $C_4$ alkyl, $C_1$ to $C_4$ alkoxy, nitro, cyano or carboxyl.

Halogen is, preferably, fluorine, chlorine and bromine. Examples of heterocyclic radicals in the abovementioned definitions are phthalimido, pyridinyl, thienyl, furyl, isoxazolyl, thiazolyl, glucopyranosyl, ribofuranosyl and oxiranyl.

The alkyl radicals of $R_1$ are preferably unsubstituted or substituted by hydroxyl, $C_1$ to $C_4$ alkoxy, mercapto, $C_1$ to $C_4$ alkylthio, halogen, nitro, amino, $C_1$ to $C_4$ alkylamino or $C_1$ to $C_6$ alkylcarbonylamino, and the substituent is preferably not on the carbon atom adjacent to the nitrogen atom.

Acyl radicals of $R_2$ are, preferably $C_1$ to $C_4$ alkylcarbonyl radicals.

Sulphonic acid radicals or $R_3$ are, preferably, $C_1$ to $C_4$ alkylsulphonyl, and phenylsulphonyl which is optionally substituted by methyl, chlorine or nitro.

Suitable bases are, for example, alkali metal hydroxides, carbonates and alcoholates and alkaline earth metal hydroxides, carbonates and alcoholates, such as KOH, NaOH, $Na_2CO_3$ and $NaOCH_3$. Any of the commercially available products can be employed as the basic ion exchangers, for example "Lewatit" M 500, M 505, M 600, MP 500 or MP 64 or "Dowex" IR 400.

The aqueous medium in the reaction consists either of water or of a water/solvent mixture, possible preferred solvents being ethers (preferably alkyl ethers) and alcohols (preferably alkanols) preferably ethanol and isopropanol. Quaternary ammonium salts, such as ammonium chloride or tetrabutylammonium chloride, can be used as auxiliaries. The reaction of the compound of formula (II) with the amine of formula (III) is generally carried out at temperatures between 50° and 250° C., and the various pressures of the solvents corresponding to the particular temperature are established in the autoclave. The reaction can be carried out either batchwise or continuously.

The intermediate products obtained before the reaction with bases or basic ion exchangers are the sulphonic acid salts of the compounds of formula (I) to be prepared according to the invention with the sulphonic acids $R_3$—$SO_3H$.

These sulphonic acid salts are obtained in a very good yield and high purity. This result was not to be expected from the state of the art.

The process described has a number of advantages. Thus, the number of reaction stages could be considerably reduced, compared with the known processes. Unstable and dangerous precursors and intermediate stages are not employed. The sulphonic acid salts enable the compounds to be prepared according to the invention to be isolated from the reaction mixture in a simple manner.

The compounds of the formula (II) are obtained from diacetone-L-sorbofuranose in a simple manner, in which, in a first step, the acyl group $R_2$ is introduced, for example by reaction with acetic anhydride, after which, in a second step and after splitting off the protective group in the 4,6-position, the product is sulphonated, for example with tosyl chloride or mesyl chloride, in a basic medium. The acetone-L-sorbofuranose of the formula

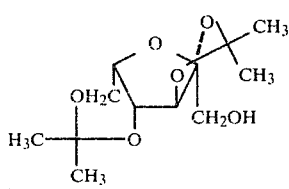

(IV)

is an intermediate product in the large-scale industrial synthesis of vitamin C, and any desired amounts thereof are thus cheaply available.

According to the present invention there is further provided sulphonic acid salts of the formula

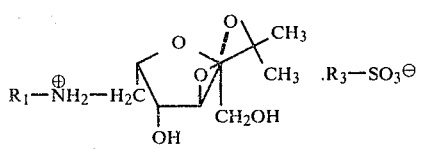

(V)

in which $R_1$ and $R_3$ have the meanings indicated above. The compounds of formula (V) are transiently formed as stable intermediate products of the process according to the invention.

$R_3$ preferably denotes p-tolyl or methyl.

According to the present invention there is further provided novel compounds of the formula

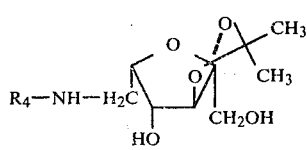

(VI)

in which $R_4$ denotes an optionally substituted alkyl, alkenyl, alkinyl or alkadienyl group.

The definition of the preferred radicals $R_4$ corresponds to the abovementioned preferred definition for $R_1$.

According to the present invention there is further provided a process for the production of compounds of the formula

(VII)

in which $R_1$ has the abovementioned meaning, in which a compound of the formula (I) is treated with acid and the product is subsequently hydrogenated. The compounds of the formula (VII) are potent inhibitors for α-glucosidases, in particular for disaccharidases (see DE-OS (German Published Specification) No. 2,758,025). They are thus suitable as medicaments against diabetes, hyperlipoproteinaemia and adiposity.

The compound of the formula (VII) in which $R_1$ is a hydrogen atom is known in the literature as 1-desoxynojirimicin.

To summarise, the invention thus in total relates to new valuable intermediate products and to a chemically unusual process for the preparation of 1-desoxynojirimicin and its N-alkyl derivatives.

The reaction of the compounds of the formula (I) to give the compounds of the formula (VII) is carried out, for example, by stirring the compounds of the formula (I) with 2 N hydrochloric acid for several hours and then hydrogenating the product in the presence of Raney nickel under 3.5 bars for several hours, triethylamine being added.

EXAMPLE 1

1.5 l of ethanol and 150 ml of water are added to 250 g of 1-O-acetyl-2,3-O-isopropylidene-6-O-tosyl-α-L-sorbofuranose (see H. Paulsen et al, loc. cit.) in a 5 liter autoclave. 750 ml of liquid ammonia are then added. The closed autoclave is heated to 140° C. for 3 hours, is then allowed to cool and is let down to normal pressure and the contents of the autoclave are concentrated to a syrup in vacuo at a bath temperature of 70° C. Thereafter, 500 ml of isopropanol are added, the mixture is cooled to 0° C., whilst stirring, and the product which had precipitated is filtered off. It is rinsed with 200 ml of isopropanol. 190.1 g (81% of theory) of the compound of the formula

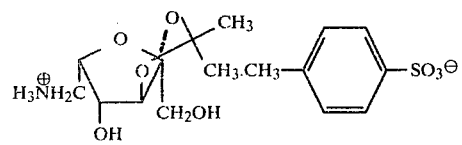

with a melting point of 202° C. are obtained.

200 g of the salt described above are dissolved in 800 ml of water at 50° C., 1,000 ml of a basic ion exchanger ("Lewatit" MP 500) are added and the mixture is stirred at 50° C. for 30 minutes. The ion exchanger is then filtered off and rinsed thoroughly with water. The aqueous filtrate is evaporated in vacuo. 101 g (90% of theory) of the free base with a melting point of 141° C. are obtained.

EXAMPLE 2

1 liter of ethanol, 80 ml of water and 400 mg of ethanolamine are added to 100 g of 2,3-O-isopropylidene-6-O-tosyl-α-L-sorbofuranose and the mixture is heated to 140° C. in an autoclave for 4 hours. Thereafter, the reaction mixture is concentrated at 100° C. and under 0.5 mm Hg, the residue is taken up in 1 liter of water and the mixture is clarified with 20 g of active charcoal. The pale yellow aqueous filtrate is stirred with 700 ml of a strongly basic ion exchanger ("Lewatit" MP 500) for 30 minutes, the ion exchanger is filtered off and the filtrate is evaporated to a syrup in vacuo. 40 g (58% of theory) of the compound of the formula

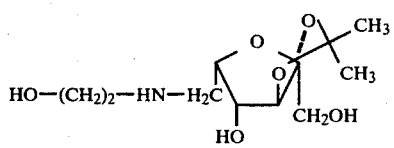

are obtained.

EXAMPLE 3

100 g of 6-amino-6-desoxy-2,3-O-isopropylidene-α-L-sorbofuranose are dissolved in 40 ml of water, and 84 ml of concentrated hydrochloric acid are slowly added at 5° C., whilst cooling. The mixture is warmed to 20° C., stirred for 2.5 hours and seeded with a few crystals of 6-amino-6-desoxy-L-sorbose hydrochloride, and 700 ml of ethanol are then added dropwise to the suspension in the course of 2 hours. The suspension is cooled to −5° C. and is stirred at this temperature for 1 hour and then filtered off. The crystals are dissolved in 700 ml of water, 10 g of 5% strength platinum-on-charcoal are added and hydrogenation is carried out at room temperature and under a pressure of 20 bars of $H_2$ in an autoclave for five hours. The solution is filtered, the filtrate is concentrated to a syrup on a rotary evaporator and the syrup is triturated with 300 ml of methanol at 50° C. The crystals are filtered off and dried. 58.8 g = 64% of theory of desoxynojirimicin hydrochloride are obtained. Melting point: 208°–210° C.

What is claimed is:

1. A process for the production of a 6-amino-6-desoxy-2,3-O-isopropyidine-α-L-sorbofuranose derivative of the formula

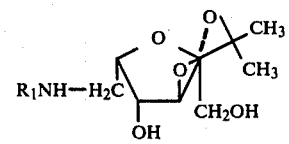

in which $R_1$ denotes a hydrogen atom or a $C_1$–$C_{18}$-alkyl, $C_2$–$C_{10}$-alkenyl, $C_2$–$C_{10}$-alkinyl or $C_2$–$C_{10}$-alkadienyl radical said $C_1$–$C_{18}$-alkyl radical being optionally substituted by hydroxyl, $C_1$–$C_4$-alkoxy, $C_1$–$C_7$-alkanoyloxy, benzoyloxy, mercapto, $C_1$–$C_4$-alkylthio, halogen, nitro, amino, $C_1$–$C_4$-alkylamino or $C_1$–$C_6$-alkylcarbonylamino, which comprises heating a compound of the formula

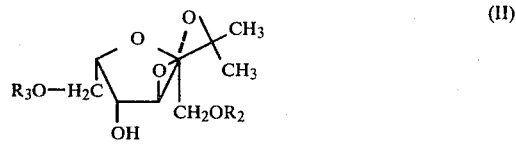

in which $R_2$ denotes a hydrogen atom or an acyl radical and
$R_3$ denotes a radical of an aliphatic or aromatic sulphonic acid, with an amine of the formula $$R_1-NH_2 \quad (III)$$

in which $R_1$ has the abovementioned meaning, in an aqueous medium in an autoclave, isolating the reaction product of the formula

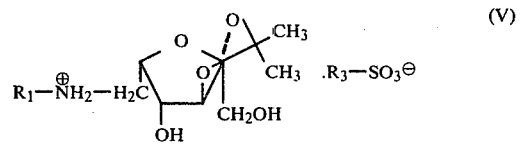

in which $R_1$ and $R_3$ have the meaning indicated above, in crystalline form and reacting the reaction product in a basic medium to give the free amine of formula (I).

2. A process according to claim 1 in which $R_1$ denotes alkyl with 1 to 18 carbon atoms or alkenyl, alkinyl or alkadienyl with 2 to 10 carbon atoms.

3. A process according to claim 1 or 2 in which the reaction of the compound of formula (II) with the amine of formula (III) is carried out at 50° to 250° C. in water or in a water/ether or a water/alcohol mixture.

4. A process according to claim 1 or 2 in which the reaction in base medium is carried with a base or a basic ion exchanger in water at room temperature to 100° C. for 10 minutes to 2 hours.

5. A compound of the formula

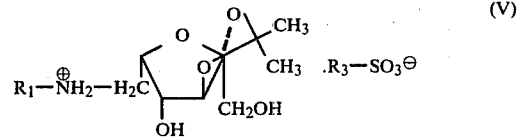

in which $R_1$ and $R_3$ have the meaning indicated in claim 1.

* * * * *